(12) United States Patent
Moran

(10) Patent No.: US 7,177,695 B2
(45) Date of Patent: Feb. 13, 2007

(54) EARLY STAGE WOUND HEALING USING ELECTROMAGNETIC RADIATION

(75) Inventor: Kelly Moran, Wilbraham, MA (US)

(73) Assignee: CefamOptec Industries, Inc., East Longmeadow, MA (US)

( * ) Notice: Subject to any disclaimer, the term of this patent is extended or adjusted under 35 U.S.C. 154(b) by 378 days.

(21) Appl. No.: 10/023,502

(22) Filed: Dec. 17, 2001

(65) Prior Publication Data

US 2003/0114884 A1    Jun. 19, 2003

(51) Int. Cl.
*A61N 5/067*    (2006.01)

(52) U.S. Cl. .............................. 607/50; 607/93; 607/89

(58) Field of Classification Search ................ 607/88, 607/89, 93, 94, 95, 100, 154, 1, 50
See application file for complete search history.

(56) References Cited

U.S. PATENT DOCUMENTS

| | | | | |
|---|---|---|---|---|
| 4,287,554 A | * | 9/1981 | Wolff | ......................... 362/218 |
| 5,259,380 A | | 11/1993 | Mendes et al. | |
| 5,344,433 A | | 9/1994 | Talmore | |
| 5,445,146 A | | 8/1995 | Bellinger | |
| 5,549,660 A | * | 8/1996 | Mendes et al. | ............... 607/88 |
| 5,766,233 A | | 6/1998 | Thiberg | |
| 6,165,205 A | * | 12/2000 | Neuberger | .................... 607/89 |
| 6,210,426 B1 | | 4/2001 | Cho et al. | |
| 6,267,779 B1 | | 7/2001 | Gerdes | |
| 6,461,866 B1 | * | 10/2002 | Whitehurst | ................. 435/325 |
| 6,471,716 B1 | * | 10/2002 | Pecukonis | .................... 607/89 |

* cited by examiner

*Primary Examiner*—Kennedy Schaetzle
(74) *Attorney, Agent, or Firm*—B J Associates; B J. Skutnik

(57) ABSTRACT

A device and method is disclosed for the treatment of early stage wounds, i.e. those wounds that have resulted in little or no breach of the skin tissue. The invention utilizes non-ablative laser or non-coherent electromagnetic radiation applied to a stage one or two wound to stimulate wound healing, destroy viral and bacterial bodies, and prevent the development of such wounds into higher stage wounds. An appropriate wavelength is chosen from the range of 193 nm to 10.6 microns, and is delivered at a power density of about at least 1 W/cm$^2$ over a predetermined treatment duration typically in the range of 1 second to 3 minutes. To achieve the desired energy density, radiation is typically delivered at a power between 1 Watt and 15 Watts, with an average power of 5–10 Watts. Early stage wounds that can be addressed with this invention include but are not limited to spider or other insect bites, bee stings, rashes, eczema, psoriasis, and poison ivy. The present invention is especially useful for patients with a compromised ability to heal or stave off infection due to diabetes or other conditions.

6 Claims, No Drawings

EARLY STAGE WOUND HEALING USING ELECTROMAGNETIC RADIATION

BACKGROUND OF THE INVENTION

1. Field of the Invention

The present invention relates to the field of applying non-ablative electromagnetic radiation to enhance wound healing during the early stages of wound development and to inhibit the progression of wounds to later stages.

2. Information Disclosure Statement

The development of wounds can be divided into four major stages. In Stage One, the skin will be warm, pink or reddened, and usually inflamed. In this stage, though the skin may look irritated, it will still be intact. In Stage Two, there is noticeable skin breakdown that is superficial in nature. At this stage, the wound may look like a blister or abrasion. In Stage Three, there is observed full thickness skin loss into the subcutaneous tissue. Finally, Stage Four represents full thickness damage to the underlying tissue, muscle, or tendons.

Current wound healing and wound debridement techniques focus exclusively on the healing of stage 3 and late stage 2 wounds, where there is true environmental exposure of subcutaneous tissue. Such wounds appear primarily as open wounds, or at a minimum appear as blisters or abrasions. There have not yet been efforts to heal wounds at their earliest stages, before such wounds mature into ulcers or other open wounds.

Low level laser therapy (LLLT), or the use of lasers of a lower power, is a technique currently used to promote wound healing. Such techniques target stage 3 and 4 wounds which are generally characterized as open wounds, blisters and ulcers. All LLLT techniques use radiation with powers of less than 1 Watt, and are generally in the range of 250 mW. LLLT devices typically deliver 10 mW–200 mW of power during treatment. LLLT treatments typically deliver power densities ranging from 0.05 $W/Cm^2$–5 $W/cm^2$ and energy densities ranging from 0.5–10 $J/cm^2$. This technique utilizes a process for wound healing known as photonic biostimulation. It is claimed that exposing an open wound to visible and infrared radiation produces observable reductions in the amount of time needed for healing.

For example, this healing stimulation technique is described in U.S. Pat. No. 5,766,233 by Thiberg, which utilizes a light-emitting diode array to deliver infrared radiation and visible red light. Pulsed infrared radiation is emitted by a large array of individual low power diodes that emit a combined total power of 900 mW over 3 minutes, followed by pulsed visible red light emitted by individual low power diodes that together produce a combined total intensity of about 3000 millicandela, with an associated power of approximately 900 mW, over 3 minutes. This invention emphasizes the need to irradiate the treatment site with both visible and infrared radiation. Furthermore, the array of low power diodes creates a beam size with a large surface area, which results in a low power density.

U.S. Pat. No. 5,259,380, by Mendes et al., discloses a low power therapy system consisting of a focused array of light-emitting diodes. It specifically discloses an array for emitting red light for wound healing with a power density on the order of 15 mW/cm2, utilizing powers between 2 and 10 mW and treatment times ranging from 7 to 20 minutes.

Another example is U.S. Pat. No. 6,267,779, which discloses an apparatus for biostimulation and treatment of tissue consisting of two focusable laser treatment wands for the continuous or pulsed emission of coincident infrared and visible radiation. Embodiments include application of laser radiation with wavelengths ranging from 400 to 700 nm and from 900 to 1100 nm. The power range runs from 0–2 W, specifying an energy of 1–99 J over treatment times ranging from 1–60 minutes. The patent claims that the intersection of the beams in the patient's body has an increased therapeutic effect.

U.S. Pat. No. 5,445,146 discloses a method for pain reduction and healing using a low level laser system with power between 100 and 800 mW with an energy density limited to the range of 1–15 $J/cm^2$.

There are many LLLT techniques for use in a variety of medical applications, but there is currently no actual proof of low level laser therapy's usefulness in stimulating tissue repair and wound healing. Though LLLT applications deliver a variety of energy densities, they often deliver the energy over long periods of time using lower radiation powers, which may be responsible for their lack of proven effectiveness.

As an alternative to LLLT, it has been shown that irradiation of an open wound with a 980 nm laser at powers of at least 5 Watts, continuously applied for a period between 10 seconds and 20 minutes or greater, is an effective method of stimulating the healing of open wounds. In a specific example disclosed in that invention, the energy density applied to a wound was approximately 33 J/cm2. See U.S. Pat. No. 6,165,205.

The present invention is unique among both low level laser therapy and other radiation treatments, in that said therapies and techniques are utilized to encourage healing exclusively in open wounds. They are not primarily applied to a wound as a preventative measure, but are used after a wound has progressed to a level where there is typically a significant breach of the skin and exposure of subcutaneous tissue to the outside environment.

Radiation treatment has also been utilized as a preventive treatment, though not directly for wound healing. U.S. Pat. No. 6,210,426 discloses a method for scar prevention following surgical procedures. A handpiece applies optical radiation to the incision 2 days to 2 months after surgery. Wavelengths between 530 and 1000 nm with energy densities ranging from 2–12 J/cm2 are used. This treatment is used to prevent the build up of scar tissue as a wound heals, but does not enhance the healing process itself.

Psoriasis and eczema are two skin conditions that often occur as Stage One or Stage Two wounds. Psoriasis is defined as a common, scaly dermatosis characterized by red and raised patches of skin. It is thought that psoriasis is caused by an overproduction of new skin cells which rise to the surface of the skin before old skin cells die and are sluffed off. This results in a break in the stratum corneum, exposing living skin cells to the environment. In early stages, psoriasis occurs as small red bumps, which can later progress to scales. Such bumps or scales can open after scratching or other irritation that can aggravate the condition and result in open wounds. There is currently no cure for psoriasis.

Eczema is defined as an itchy dermatosis caused by a variety of factors, and is characterized by a redness of the skin due to an overconcentration of capillaries, oedema (the presence of abnormally large amounts of fluid in the intercellular tissue spaces of the skin), and crusting or scaling of the skin in more chronic cases. Later stages of the disease, or scratching by the patient, can result in skin that is broken, raw or bleeding.

Methods are known for treating psoriasis and eczema, though these methods are concerned with treating open wounds or sores associated with these conditions. Included among these methods is treatment of psoriasis with electromagnetic radiation. Talmore, in U.S. Pat. No. 5,344,433, describes a method for treating "psoriasis skin wounds" with high intensity ultraviolet and infrared radiation, produced by a lamp, focused with a lens, and delivered through a liquid light guide with a minimum irradiance of 1 mW/cm$^2$.

There is a need for a method to treat wounds at their earliest stages, including early stages of eczema and psoriasis, and stimulate healing before such wounds progress into larger or deeper wounds. In particular, a method for healing psoriasis while it is still in its early stages (when symptoms are limited to red bumps or scales, and are not yet open sores) would be extremely useful in stopping the spread of psoriasis to other parts of the body. The present invention fills this need.

OBJECTIVES AND BRIEF SUMMARY OF THE INVENTION

It is an object of the present invention to provide a method for the healing of early stage wounds with non-ablative electromagnetic radiation.

It is another object of this invention to provide a method for the healing of early stage wounds in those patients who have diabetes, other conditions that inhibit natural wound healing, or other conditions that would accelerate the progression of a wound to stage 3 or 4.

It is a further object of this invention to provide a method capable of preventing early stage wounds such as rashes, spider or mosquito bites, acne, poison ivy, or other skin conditions from advancing to higher stages and developing into open wounds or sores.

It is yet a further object of the present invention to provide a method capable of stimulating the healing of psoriasis and eczema as early stage wounds.

It is yet another object of the present invention to provide a method capable of relieving discomfort associated with early stage wounds, and thus preventing scarring that could occur during the healing process or as a result of scratching or other irritation.

Briefly stated, the present invention provides a method for the healing of early stage wounds, i.e. those wounds that have resulted in little or no breach of the skin tissue or stratum corneum. The invention utilizes non-ablative laser or non-coherent electromagnetic radiation applied to an early stage wound to stimulate wound healing, destroy viral and bacterial bodies, and prevent the development of such wounds into higher stage wounds. An appropriate wavelength is chosen from the range of 193 nm to 10.6 microns, and is delivered at a power density of at least about 1 W/cm$^2$ over a predetermined treatment duration typically in the range of 1 second to 3 minutes. To achieve the desired energy density, radiation is typically delivered at a power between 1 Watt and 15 Watts, with an average power of 5–10 Watts. Early stage wounds that can be addressed with this invention include red and inflamed patches of skin that have the potential to develop into more serious wounds. Such early stage wounds include but are not limited to spider or other insect bites, bee stings, rashes, eczema, acne, psoriasis, and poison ivy. The present invention is especially useful for patients with a compromised ability to heal or to stave off infection due to diabetes or other conditions.

The above, and other objects, features and advantages of the present invention will become apparent from the following description.

DETAILED DESCRIPTION OF PREFERRED EMBODIMENTS

The present invention is a method for the use of high powered non-ablative radiation for the healing of early stage wounds and for the prevention of the progression of such wounds into open sores or breaks in the skin. In particular, radiation with a wavelength within the range of 193 nm to 10.6 microns is delivered to an early stage wound to stimulate healing. Radiation with a wavelength in the range of 193 mn to 3 microns is preferred. This radiation can be coherent, such as a laser beam, or non-coherent, such as radiation emitted from a lamp. Such non-ablative radiation is delivered at a power density of about at least 1 W/cm$^2$ over a predetermined treatment duration typically in the range of 1 second to 3 minutes. To achieve the desired power density, radiation is typically delivered at a power between 1 Watt and 15 Watts, with an average power of 5–10 Watts. This use of electromagnetic radiation is novel in that it is applied as both a healing and a preventive measure.

Although the actual cause of wound healing acceleration after application of high power radiation is not exactly known, it is thought that application of such laser or incoherent radiation encourages healing by inducing a number of processes in the skin. Radiation causes vasculation, or the growth of new blood vessels in the treatment area. It also stimulates the growth of fibroblasts, which in turn produce collagen to promote tissue growth. An additional benefit of the present invention is its ability to eradicate bacteria in the treatment site, thus preventing infection that could exacerbate the wound and cause it to develop into a more serious wound.

The present method can be accomplished with a variety of embodiments and apparatuses. Both laser and non-coherent non-ablative radiation can be used. Possible delivery means include, but are not limited to, bare fibers, collimated delivery systems, or direct radiation from diodes and lamps.

The present invention is effective for early stage wounds such as spider bites or other insect bites, bee stings, rashes, eczema, psoriasis and poison ivy. During the healing stimulation process, such irradiation has been shown to relieve itching, diminish oedema, and prevent scarring. In particular, the presence of oedema in skin conditions such as poison ivy has proven beneficial to the healing effect of the present invention. Unlike other treatments such as those utilizing $CO_2$ or Erbium lasers that are highly absorbed in water, fluid trapped in the unbroken skin wound seems to facilitate the transmission and improve the healing effects of the treatment radiation as applied with the given method.

In contrast to most other treatment modalities, the present method is equally effective for and particularly beneficial to diabetics and other patients with conditions that would normally either inhibit wound healing or accelerate the progression of a wound to stage 3 or 4. For those patients who suffer from such conditions, even seemingly minor skin irritations or redness could progress into a major wound. The present invention can prevent this from occurring. Most other treatment methods focus on either diabetic patients or non-diabetic patients, and cannot treat both equally well. In diabetics, who often suffer from a lack of proper circulation, irradiation with the present device and method can prevent infection while simultaneously inducing vascular growth.

The present invention is further illustrated by the following examples, but is not limited thereby.

EXAMPLE 1

Treatment of Insect Bite:

A 980 nm wavelength laser is delivered to a treatment site by means of a bare fiber with a 1000 micron core. The fiber tip is held 1 cm away from the surface of the skin. The laser power is set at 3 Watts, which translates to effective power incident upon treatment surface equal to 1.92 W. The insect bite is subjected to a single treatment, consisting of continuous wave irradiation for 3 seconds. At the above distance, the circular spot size of the laser has a 0.68 cm diameter, with a corresponding area of 0.363 $cm^2$. This translates into a power density of 5.29 $W/cm^2$. Over 3 minutes, the energy density delivered equals 15.87 $J/cm^2$.

In addition to reduced healing time, itching and swelling are eliminated if the wound was not scratched or otherwise irritated before treatment. If the patient agitated the wound by scratching before treatment, the treatment will still relieve itching, but its ability to reduce or prevent swelling is compromised.

EXAMPLE 2

Treatment of Poison Ivy:

A poison ivy rash was successfully treated with radiation as described in the present invention and in this example. 980 nm laser radiation, delivered through a bare fiber tip, was used to irradiate the treatment site. The fiber had a 1000 micron core, and radiation was delivered with a power of 25 Watts. A power density of approximately 44 $Watts/cm^2$ is incident on the treatment site.

One treatment was applied, with the laser painted on the rash for a period of time sufficient to heat the area until it approximates the temperature of sunburned skin. The rash after one treatment was completely cleared up after 10 days. Not only did the treatment reduce the healing time, but it also relieved itching. This has the added benefit of preventing irritation of the rash by the patient through scratching, which could further delay healing. This method resulted in complete healing within a 10 day period after a single brief treatment, in contrast to the typical treatment modalities that heal rashes in approximately the same time but require repeated daily topical treatments.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method to prevent wound progression and enhance wound healing for stage 1 and stage 2 wounds by irradiating said stage 1–2 wound with directed non-ablative coherent radiation operating at one or more wavelengths around 980 nm, wherein said method uses at least one optical fiber connected to a source of coherent radiation to irradiate said wound.

2. A method to prevent wound progression and enhance wound healing according to claim 1, wherein said method uses non-ablative coherent radiation having a power density of at least about 1 $W/cm^2$ for a preselected time of exposure in a range from 1 second to 3 minutes.

3. A method to prevent wound progression and enhance wound healing according to claim 2, wherein said method uses non-ablative coherent radiation operating at about 980 nm.

4. A method to prevent wound progression and enhance wound healing according to claim 2, wherein said method uses non-ablative radiation having an average power between 1 Watt and 20 Watts.

5. A method to prevent wound progression and enhance wound healing according to claim 2, wherein said method uses non-ablative coherent radiation preferably having an average power between 5 and 10 W.

6. A method to prevent wound progression and enhance wound healing according to claim 1, wherein said method also includes eradicating bacteria and viral bodies, thereby preventing infection.

* * * * *